United States Patent
Lager

(10) Patent No.: US 9,707,040 B2
(45) Date of Patent: Jul. 18, 2017

(54) SURGICAL DRAPE OR TOWEL HAVING AN ADHESIVE EDGE

(75) Inventor: Katarina Lager, Sävedalen (SE)

(73) Assignee: Mölnlycke Healthcare AB, Göteborg (SE)

( * ) Notice: Subject to any disclaimer, the term of this patent is extended or adjusted under 35 U.S.C. 154(b) by 417 days.

(21) Appl. No.: 13/809,025

(22) PCT Filed: Jul. 5, 2011

(86) PCT No.: PCT/SE2011/050907
§ 371 (c)(1),
(2), (4) Date: Jan. 8, 2013

(87) PCT Pub. No.: WO2012/005674
PCT Pub. Date: Jan. 12, 2012

(65) Prior Publication Data
US 2013/0104908 A1    May 2, 2013

Related U.S. Application Data

(60) Provisional application No. 61/362,714, filed on Jul. 9, 2010.

(30) Foreign Application Priority Data

Jul. 9, 2010   (SE) ...................... 1050775

(51) Int. Cl.
*A61B 46/00*   (2016.01)
*A61B 19/08*   (2006.01)
*A61B 46/20*   (2016.01)

(52) U.S. Cl.
CPC ............ *A61B 19/088* (2013.01); *A61B 46/00* (2016.02); *A61B 46/40* (2016.02); *A61B 2046/205* (2016.02)

(58) Field of Classification Search
CPC ...................................... A61F 13/00
USPC ................. 128/851, 849, 846, 852, 850
See application file for complete search history.

(56) References Cited

U.S. PATENT DOCUMENTS

| 3,364,928 A | * | 1/1968 | Creager, Jr. | ............ A61B 46/30 |
| | | | | 128/853 |
| 3,669,106 A | | 6/1972 | Schrading | ...................... 128/132 |
| 3,930,497 A | * | 1/1976 | Krebs | ..................... A61B 46/00 |
| | | | | 128/853 |

(Continued)

FOREIGN PATENT DOCUMENTS

| CN | 1642491 | 7/2005 |
| CN | 101102726 | 1/2008 |

(Continued)

OTHER PUBLICATIONS

Translation of foreign patent SE502934.*

(Continued)

*Primary Examiner* — Tarla Patel
(74) *Attorney, Agent, or Firm* — Ballard Spahr LLP

(57) ABSTRACT

Provided is a surgical drape or towel comprising a base sheet composed of one or more layers. An edge region of the base sheet has a recess therein and the recess is covered by a strip of thin plastic film having a layer of adhesive on one side thereof for attaching the surgical drape or towel to skin.

14 Claims, 1 Drawing Sheet

(56) References Cited

U.S. PATENT DOCUMENTS

| | | | | |
|---|---|---|---|---|
| 4,206,945 A | * | 6/1980 | Kifferstein | B60N 2/6036 |
| | | | | 297/220 |
| 4,413,624 A | * | 11/1983 | Snow | A61F 6/02 |
| | | | | 128/842 |
| 4,520,807 A | * | 6/1985 | Rotter | A61B 17/42 |
| | | | | 128/849 |
| 4,889,136 A | * | 12/1989 | Hanssen | A61B 46/00 |
| | | | | 128/849 |
| 4,901,714 A | * | 2/1990 | Jensen | A61F 13/0203 |
| | | | | 128/846 |
| 5,647,376 A | * | 7/1997 | Thompson | A61B 46/00 |
| | | | | 128/853 |
| 5,794,276 A | * | 8/1998 | Walker | A41D 13/11 |
| | | | | 128/202.19 |
| 5,871,014 A | * | 2/1999 | Clay | A61B 46/30 |
| | | | | 128/849 |
| 2005/0284487 A1 | | 12/2005 | Gellerstedt | 602/52 |
| 2006/0124138 A1 | | 6/2006 | Dusenbery | 128/849 |

FOREIGN PATENT DOCUMENTS

| | | |
|---|---|---|
| SE | 502934 | 12/1995 |
| SE | 502934 | 2/1996 |
| WO | WO 96/00045 | 1/1996 |
| WO | WO 96/01594 | 1/1996 |
| WO | WO 03/079919 | 10/2003 |
| WO | WO 2006/075946 | 7/2006 |
| WO | WO 2008/054312 | 5/2008 |
| WO | WO 2012/005674 | 1/2012 |

OTHER PUBLICATIONS

Written Opinion issued on Oct. 14, 2011 for International Patent Application No. PCT/SE2011/050907, which was filed on Jul. 5, 2011 [Inventor—Lager; Applicant—Mölnlycke Health Care AB] [5 pages].

International Search Report issued on Oct. 14, 2011 for International Patent Application No. PCT/SE2011/050907, which was filed on Jul. 5, 2011 [Inventor—Lager; Applicant—Mölnlycke Health Care AB] [5 pages].

Response to International Search Report and Written Opinion filed on Feb. 27, 2012 for International Patent Application No. PCT/SE2011/050907, which was filed on Jul. 5, 2011 [Inventor—Lager; Applicant—Mölnlycke Health Care AB] [2 pages].

International Preliminary Report on Patentability issued on Jan. 15, 2013 for International Patent Application No. PCT/SE2011/050907, which was filed on Jul. 5, 2011 [Inventor—Lager; Applicant—Mölnlycke Health Care AB] [6 pages].

Supplementary European Search Report issued on Aug. 7, 2012 by the European Patent Office for International Patent Application No. EP 20110803903, which was filed on Jul. 5, 2011 [Inventor—Lager; Applicant—Mölnlycke Health Care AB] [3 pages].

Communication Pursuant to Article 94(3) EPC issued on Oct. 19, 2012 by the European Patent Office for International Patent Application No. EP 20110803903, which was filed on Jul. 5, 2011 [Inventor—Lager; Applicant—Mölnlycke Health Care AB] [4 pages].

* cited by examiner

SURGICAL DRAPE OR TOWEL HAVING AN ADHESIVE EDGE

CROSS-REFERENCE TO RELATED APPLICATIONS

The present application is a U.S. National Phase Application of International Application No. PCT/SE2011/050907, filed Jul. 5, 2011, which claims priority to Swedish Patent Application No. 1050775-4, filed Jul. 9, 2010, and U.S. Patent Application No. 61/362,714, filed Jul. 9, 2010, all of which applications are incorporated herein fully by this reference.

TECHNICAL FIELD

The present invention relates to a surgical drape or towel comprising a base sheet composed of one or more layers.

BACKGROUND OF THE INVENTION

Surgical drapes or towels do often have an adhesive edge, i.e. an adhesive coating along the whole or part of an edge, in order to enable a draping of one or more surgical drapes or towels around an operation site on a body of a patient, in which site a surgical intervention is to be performed. A function of such an adhesive edge is to form a barrier preventing liquid from the operation site to flow in under the surgical drape or towel or bacteria from outside the operation site to enter the operation site from the area under the surgical drape or towel. It can be hard to ensure that such a barrier is leak proof for operation sites on obese patients or on operation sites on curved portions of the body of a patient, e.g. ears, nose, neck and breasts of a patient since the adhesive edge of commercial available surgical drapes or towels can not follow the body contour around the operation sites. In order to solve this problem WO 2008/054312 discloses a surgical drape in which the adhesive edge of the drape consists of a thin plastic film projecting out from the rest of the drape which on one side is coated with an adhesive and on the opposite side has a stiffening strip which is to be removed after application of the drape. The stiffening strip is necessary for enabling handling and application of the drape after removal of a release layer protecting the adhesive coating before application of the drape. However, the application of such a drape is complicated and includes many steps and it is not unusual that portions of the film attach to each other thereby forming folds that increase risk for leakage. Furthermore, it is from a production point of view also complicated to apply such a film along the edge of a base drape.

The objective of the present invention is to provide a surgical drape or towel having an adhesive edge, which is easy to apply, very flexible and stretchable at least in the area of an operation site and relatively easy to produce.

SUMMARY OF THE INVENTION

This objective is accomplished by a surgical drape or towel comprising a base sheet composed of one or more layers, characterized in that an edge region of said base sheet has a recess therein and that said recess is covered by a strip of thin plastic film having a layer of adhesive on one side thereof for attaching the surgical drape or towel to skin. The edge regions of the surgical drape or towel on both sides of the recess functions as handles enabling easy application of the edge region containing the strip of thin plastic film along a border of the operation site also after removal of the release layer on the strip of thin plastic film. The thin plastic film is very flexible and can follow any curved contour of the body of a patient and also irregularities in the skin of the patient. Furthermore, the thin plastic film is stretchable which facilitates application to curved contours and to irregularities in the skin and also enables an attached adhesive edge to follow any stretching of the skin occurring after application of the surgical drape or towel.

In the preferred embodiment, the weight per unit area of the plastic film is 10-60 $g/m^2$, preferably 10-50 $g/m^2$, more preferably 20-30 $g/m^2$, most preferably 25 $g/m^2$.

Said recess has a depth of 0.5-20 cm, preferably 1-10 cm and a width of 3-120 cm, preferably 5-90 cm.

The adhesive layer on one side of the strip of thin plastic film covering said recess can consist of acrylate adhesive or a silicone gel adhesive.

Said base sheet is preferably coated with an adhesive in edge regions on both sides of said recess. These adhesive coatings can comprise the same adhesive as the coating on the strip of thin plastic film covering the recess or another adhesive.

The strip of thin plastic film covering said recess is preferably made of polyethylene.

Each adhesive layer along the edge having said recess is protected by a release layer which is removed before application of the surgical drape or towel. The release layer protecting the adhesive layer on the strip of thin plastic film covering said recess can consist of one or more pieces.

BRIEF DESCRIPTION OF THE DRAWING

The invention will now be described with reference to the enclosed figures, of which.

DESCRIPTION OF EMBODIMENTS

Figure 1:
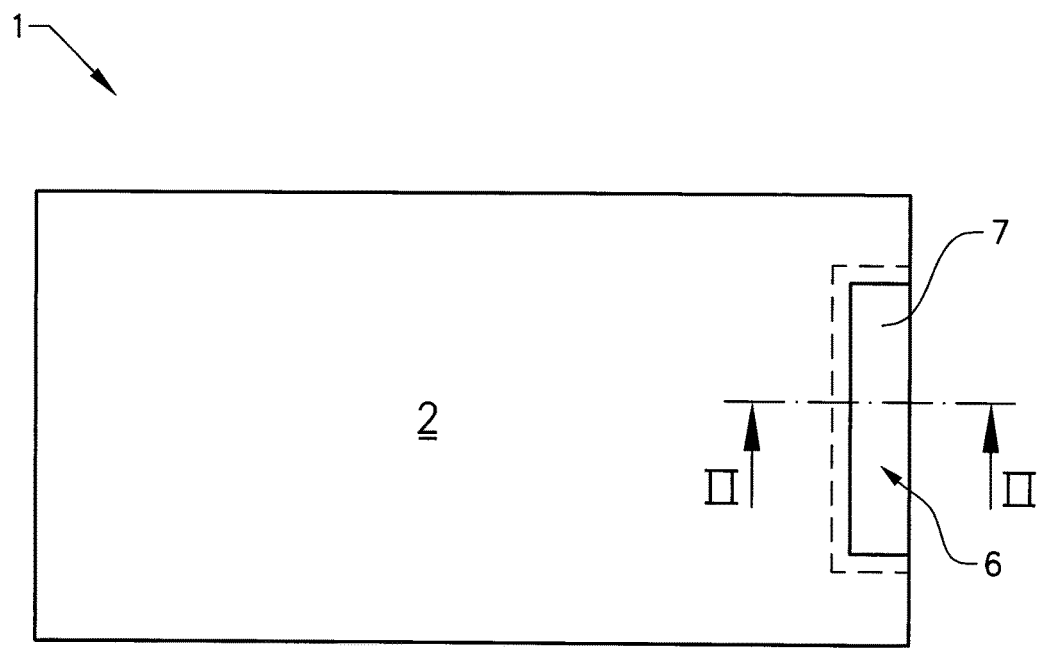
FIG. 1 schematically discloses a surgical drape according to a preferred embodiment of the invention, FIG. 2 discloses a sectional view along line II-II in FIG. 1.
Figure 2:
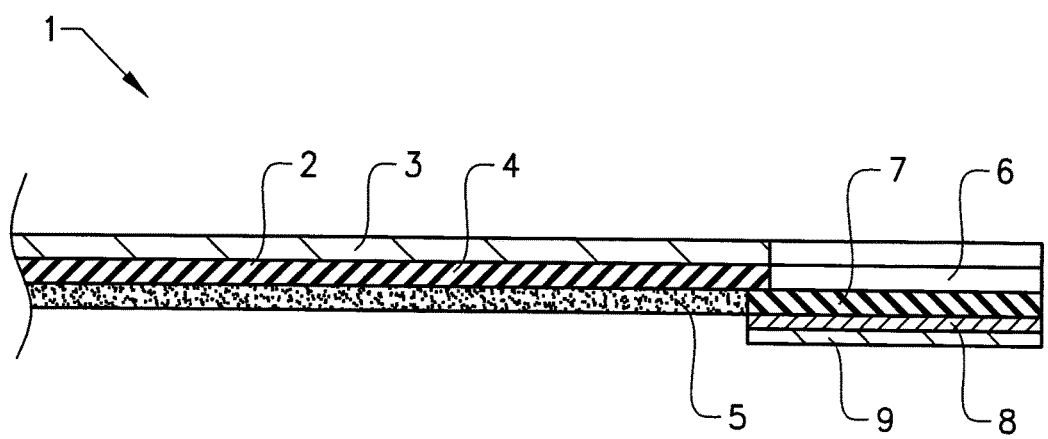

In FIGS. 1 and 2 a preferred embodiment of a surgical drape 1 with an adhesive edge is schematically shown. The surgical drape 1 comprises a base sheet 2, which is composed of three layers laminated to each other. The upper layer 3, consists of an absorbent material, such as a nonwoven, and functions to absorb blood or other liquid from an operation site in order to prevent this liquid from coming in contact with the operating personnel or running off the drape. The upper layer is distal from the body of a patient when the drape is used. The intermediate layer 4 consists of a liquid impermeable material, such as a plastic film, for example polyethylene, and functions as a barrier to prevent liquid from an operation site to come in contact with the body of a patient outside of the operation site. The lower layer 5, in use proximal to the skin of a patient, functions as a comfort layer by providing a soft and comfortable contact surface and can consist of a nonwoven, a wadding or other soft skin friendly materials. However, although a three-layered drape material is preferred, other drape materials having one or more layers, such as a one-layered drape of textile material, can be used in the present invention.

A recess 6 is cut out in an edge region of the base sheet 2 and a strip 7 of thin plastic film with a first side and a second side opposite from the first side covering the area of the recess is affixed to the base sheet 2. The lower side (first side) of the strip 7 is covered with a layer 8 of a skin friendly adhesive and the layer 8 of adhesive is in turn covered by release layer 9, which is to be removed before application of the surgical drape 1.

During application of the surgical drape 1, the edge regions of the base sheet 2 on both sides of recess 6 and proximal thereto functions as a sort of handles enabling the person applying the surgical drape to hold the strip 7 of thin plastic film tensed during the application of this strip onto the skin of a patient. This tension is necessary in order to prevent possible folds in base sheet 2 from reaching said bottom edge and thereby also the strip 7. If folds occur in the strip 7, there is a risk that such folds remain after application of the surgical drape 1 thereby weakening the barrier provided by the strip 7 when attached to the skin of a patient. By "holding the strip tensioned" is meant that the force used is large enough to ensure that no slackening of the strip 7 occur but not so large that any or at least no significant elongation of parts of the stretchable strip 7 takes place.

If the border of the operation site along which the strip 7 shall be attached has a complicated shape, the application of the strip 7 is preferably made stepwise. Firstly, an end part of the strip 7, i.e. a part proximal to one of the short sides of the recess 6, is attached to the skin of the patient and anchored thereto by pressing thereon with one hand while maintaining the tensioning of the strip. Thereafter, the grip of the edge region of the base sheet 2 proximal to the anchored end part of strip 7 is released and the then provided free hand is made to closely follow the contour of the body of the patient and simultaneously press the strip 7 to the skin of the patient. At the same time the tension of the strip is maintained by the other hand. Such a way of application of the strip has the advantage that the strip can be applied without stretching thereof which is very hard to obtain for a strip having a releasable stiffening layer on its upper side as the drape known from WO 2008/054312 in which the flexibility of the adhesive edge is dependent on the flexibility of the stiffening layer in the initial stage of the application thereof. After removal of the stiffening layer after application of the known adhesive edge along a border of an operation site, the stretchability of the plastic film makes it possible to locally press the film into tight contact with the skin along the border of the operation site. If such a border has a complicated shape it is thus necessary to again press the adhesive edge against the border of the operation site after removal of the stiffening layer in order to ensure that this edge along its entire length closely follows the contour of the body of the patient.

The application of the surgical drape 1 can be made in other ways than described above. Such drapes are stored folded and can thus be applied by first fasten the area of the strip 7 in the fold at a suitable point of the border of the operation site and then successively fasten the strip on one or both sides of the fold during simultaneous unfolding of the drape.

During some types of operations the skin is considerably stretched and it is important that the adhesive edge can be stretched along with the skin in order not to irritate or damage the skin or to prevent the adhesive edge from loosening from the skin. Since principally all the stretchability of the strip 7 in the surgical drape 1 disclosed in FIGS. 1 and 2 can be maintained after application thereof, the described surgical drape is very suitable to use for the draping of a patient being subjected to such an operation.

The base sheet 2 is preferably a commercially available drape, such as Barrier® available from Mölnlycke Health Care AB, Gothenburg, Sweden, in which the recess 6 is cut out.

The strip 7 of plastic film has preferably a weight per unit area of 10-60 $g/m^2$, preferably 10-50 $g/m^2$, more preferably 20-30 $g/m^2$, most preferably 25 $g/m^2$ and is preferably made of polyethylene. However, other plastic materials, such as polyurethane can also be used. In the embodiment shown in FIGS. 1 and 2, the strip 7 is affixed to the intermediate layer 4 of base sheet 2 in order to ensure that liquid from an operation site can not enter under the sheet 2 through the comfort layer 5. The strip 7 is affixed to the intermediate layer 4 in any suitable way, such as by a glue or welding seam.

The adhesive layer 8 consists preferably of a soft acrylate adhesive or a silicone gel adhesive. Such adhesive layers are stretchable and can follow the possible stretching of the strip 7. Furthermore, such adhesive layers can be removed from skin without damage thereto and without causing pain to a patient. However, also other adhesives used for adhesive edges on surgical drapes can be used in the present invention.

The length of the recess 6, i.e. the distance between the short sides of the recess should be 3-120 cm, preferably 5-90 cm and the depth thereof, i.e. the distance between the edge of strip 7 coincident with an edge of the drape 1 and the bottom edge of the recess 6, should be 0.5-20 cm, preferably 1-10 cm.

The edge regions of the surgical drape 1 on both sides of the recess 6 can also be provided with an adhesive coating (not shown in the figures). Such a coating is preferably affixed to the intermediate layer of the drapes but this is not necessary since these regions are not applied along a border of an operation site. The function of such adhesive coating is to take up part of the loads the drape is subjected to. In this respect it is pointed out that the relationship between the length of the recess and the combined length of the edge regions on both sides of the recess can be different from the relationship shown in the figures so that these edge regions can take up a considerable part of the loads on the drape. The adhesive coated on these regions can be different from the adhesive coated on the strip 7.

The release layer should be easy to remove from the adhesive layers and should be able to be removed without deteriorating the properties of the adhesive. The release layer is therefore chosen dependent on the adhesive used. A commonly used release layer consists of silicone coated paper or plastic film but such a material can not be used for silicone gel adhesive for which a plastic material, such a polyethylene, can be used.

The release layer can consist of one or more pieces of release material. If the strip 7 is long, the release layer 9 preferably consists of several pieces, thereby enabling successive application of strip 7 by removal of a first piece of release material, attaching the part of the strip from which the first piece of release material has been removed to the skin of the patient, removal of a second piece of release material, attaching of the part of the strip 7 from which the second piece of release material has been removed to the skin of the patient, and so on until the whole strip 7 has been attached along a border of an operation site.

The described embodiments can of course be modified without leaving the scope of invention, for example applied to other types of surgical drapes or towels than shown in the figures. For example can the adhesive edges of the surgical drape be edges of a slit in the surgical drape. The strip of thin plastic film can be affixed to the upper side of the liquid impermeable layer of the drape instead of the lower side thereof. The strips of thin plastic film are preferably transparent but semi-transparent or opaque films can be used. The scope of protection shall therefore only be restricted by the content of the enclosed patent claims.

The invention claimed is:

1. A surgical drape comprising a base sheet composed of three layers laminated to each other consisting of an upper layer of absorbent material, an intermediate layer of a liquid impermeable material, and a lower layer, wherein an edge region of said base sheet has a cut-out recess therein through the three layers, wherein said base sheet composed of the three layers is additionally coated with a layer of adhesive in both edge regions on opposing sides of said cut-out recess, wherein the layer of adhesive in both edge regions on opposing sides of said cut-out recess is configured to directly attach to skin, and wherein said cut-out recess is covered by a strip of thin plastic film that is affixed to the base sheet, wherein the strip of thin plastic film covering the cut out recess has a tension that reduces the risk of folds occurring in the strip of thin plastic film during the application of the surgical drape, wherein the strip of thin plastic film has a first side and a second side opposite from the first side, wherein the first side of the thin plastic film has a layer of adhesive that is configured to directly attach to skin, thereby attaching the surgical drape to the skin during use.

2. The surgical drape according to claim 1, wherein the strip of thin plastic film has a weight per unit area of 10-60 g/m$^2$.

3. The surgical drape according to claim 2, wherein said cut-out recess has a depth of 0.5-20 cm.

4. The surgical drape according to claim 3, wherein the adhesive layer on the first side of the strip of thin plastic film covering said cut-out recess consists of silicone gel adhesive.

5. The surgical drape according to claim 3, wherein the adhesive layer on the first side of the strip of thin plastic film covering said cut-out recess consists of acrylate adhesive.

6. The surgical drape according to claim 2, wherein said cut-out recess has a depth of 1-10 cm.

7. The surgical drape according to claim 2, wherein said cut-out recess has a width of 3-120 cm.

8. The surgical drape according to claim 2, wherein said cut-out recess has a width of 5-90 cm.

9. The surgical drape according to claim 1, wherein the strip of thin plastic film covering said cut-out recess is made of polyethylene.

10. The surgical drape according to claim 1, wherein the layer of adhesive on the first side of the strip of thin plastic film is protected by a release layer which is removed before application of the surgical drape.

11. The surgical drape according to claim 10, wherein the release layer protecting the layer of adhesive on the first side of the strip of thin plastic film comprises one or more pieces.

12. The surgical drape according to claim 1, wherein the strip of thin plastic film has a weight per unit area of 10-50 g/m$^2$.

13. The surgical drape according to claim 1, wherein the strip of thin plastic film has a weight per unit area of 20-30 g/m$^2$.

14. The surgical drape according to claim 1, wherein the strip of thin plastic film has a weight per unit area of 25 g/m$^2$.

* * * * *